United States Patent [19]

Kline

[11] 4,165,333

[45] Aug. 21, 1979

[54] ANTIOXIDANTS

[75] Inventor: Richard H. Kline, Cuyahoga Falls, Ohio

[73] Assignee: The Goodyear Tire & Rubber Company, Akron, Ohio

[21] Appl. No.: 879,533

[22] Filed: Feb. 21, 1978

[51] Int. Cl.$^2$ .................... C07C 153/11; C08F 4/40; C08F 4/34; C08F 22/24
[52] U.S. Cl. .................... 260/455 R; 526/94; 526/230; 526/286
[58] Field of Search .................... 260/455 R

[56] References Cited

U.S. PATENT DOCUMENTS 3,714,122  1/1973  Kline .................... 260/593 R

*Primary Examiner*—John M. Ford
*Assistant Examiner*—Robert C. Whittenbaugh
*Attorney, Agent, or Firm*—J. Y. Clowney

[57] ABSTRACT

Antioxidants such as S-[3-(3,5-ditert.-butyl-4-hydroxyphenyl) propyl] thiomethacrylate are used to stabilize polymers either by being physically incorporated therein or by being polymerized in combination with other monomer to form polymers with built-in antioxidant protection.

3 Claims, No Drawings

ANTIOXIDANTS

This invention relates to age resisters and age resistant polymeric compositions as well as a process for preparing said age resistant polymeric compositions. More particularly the invention relates to polymeric compositions that possess resistance to oxidative aging even after said compositions have been subjected to solvents which would extract at least a portion of many conventional age resisters when used to stabilize polymeric compositions.

Essentially all types of rubber, both natural and synthetic, and particularly rubbers formed from dienes, are known to be susceptible to deterioration resulting from prolonged exposure to oxidative aging. Unfortunately many of the commercially accepted stabilizers may be volatilized when the polymeric products are exposed to elevated temperatures and/or high vacuum over prolonged periods of time. Furthermore, they are rather quickly extracted from polymeric compositions by repeated washings with aqueous detergent solutions or organic solvents. These severe conditions are routinely encountered by garments containing rubber when they are subjected to frequent laundering or drycleaning.

Attempts to remedy these problems are disclosed in references such as U.S. Pat. Nos. 3,714,122; 3,953,402: 3,962,187; 3,645,970; German Pat. No. 1,931,452; Canadian Pat. Nos. 955,349 and 979,594. Other phenolic antioxidants are desired which also provide solutions to these problems.

It is therefore an object of this invention to provide age resisters and polymeric compositions that are resistant to oxidative aging. It is another object of this invention to provide a process for preparing age resistant polymeric compositions. Other objects will become apparent as the description proceeds.

In accordance with the present invention age resistant polymeric compositions are prepared by polymerizing a phenolic age resister with one or more comonomers. The phenolic age resister which can be so used has the following structural formula:

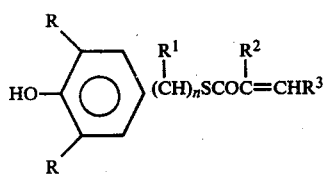

wherein R is a tertiary alkyl radical containing 4 to 8 carbon atoms, $R^1$ and $R^3$ are selected from the group consisting of hydrogen, alkyl radicals containing 1 to 4 carbon atoms and phenyl radicals, $R^2$ is selected from the group consisting of hydrogen and alkyl radicals containing 1 to 4 carbon atoms and wherein n is 1 to 12.

The term "phenyl radicals" as used herein is intended to describe phenyl and substituted phenyl radicals containing one or two alkyl substituents containing 1 to 4 carbon atoms.

In a given compound the R radicals may be the same or different. When n is greater than 1 the $R^1$ radicals can be the same or different.

Preferably R is tert. butyl, $R^1$ is hydrogen, $R^2$ is methyl or hydrogen, $R^3$ is hydrogen and n is 1 to 3.

Compounds of the present invention are illustrated by combining the radicals listed below.

| R | $R^1$ |
|---|---|
| tert.butyl | hydrogen |
| tert.amyl | methyl |
| 1,1-dimethylbutyl | ethyl |
| 1,1-dimethylpentyl | propyl |
| 1,1,3-trimethylbutyl | butyl |
| 1,1,3,3-tetramethylbutyl | phenyl |
| 1,1-dimethylhexyl | p-tolyl |
|  | p-tert.butylphenyl |

| $R^2$ | $R^3$ |
|---|---|
| hydrogen | hydrogen |
| methyl | methyl |
| ethyl | ethyl |
| propyl | propyl |
| isopropyl | butyl |
| butyl | phenyl |
| sec.butyl | p-tolyl |
|  | p-tert.butylphenyl |

One of the methods by which the thioesters of this invention can be prepared is by adding an anhydride or an acid chloride of an α-β-unsaturated carboxylic acid to a solution of a 3,5-di-tert.-alkyl-4-hydroxyphenyl (alkyl) mercaptan and an acid acceptor, such as a pyridine or triethylamine, in an aprotic solvent such as ethyl ether, tetrahydrofuran, carbon tetrachloride, or pyridine, which may serve as both solvent and acid acceptor. The reaction is normally carried out at ambient temperature, but can be accomplished at any desired temperature between 0° C. and the boiling point of the solvent.

The aforementioned monomeric age resisters may be polymerized by well known free radical polymerization techniques with one or more comonomers that are known to polymerize in free radical initiated polymerization systems. The polymerization may be carried out in emulsion, suspension, bulk or solution type systems.

Examples of free radical initiators that are useful in the practice of this invention are those known as "Redox" initiators, such as appropriate combinations of chelated iron salts, sodium formaldehyde sulfoxylate and organic hydroperoxides such as cumene and paramenthane hydroperoxides. Other initiators such as azoisobutyronitrile, benzoyl peroxide, hydrogen peroxide and potassium persulfate may also be used, depending on the particular polymerization system.

Examples of comonomers that are useful in the practice of this invention are polymerizable unsaturated hydrocarbons, both substituted and unsubstituted, including conjugated diene monomers, such as butadiene-1,3; 2-chlorobutadiene-1,3; isoprene; 2-ethyl-butadiene-1,3; 2,3-dimethyl butadiene-1,3; piperylene; and hexadienes and copolymerizable monoolefins including vinyl and vinylidene monomers such as styrene, α-methylstyrene, divinyl benzene, vinyl chloride, vinyl acetate, vinylidene chloride, methylmethacrylate, ethylacrylate, the vinylpyridines including 2-vinyl pyridine, 5-methyl-2-vinylpyridine, 4-vinyl pyridine and 2-vinyl-5-ethyl pyridine, acrylonitrile, methacrylonitrile, methacrylic acid and acrylic acid. The monomer charge weight ratio is normally from about 0.10/99.9 to about 10/90 or even 20/80 monomeric age resister/comonomer. A charge ratio of about 0.5/99.5 to about 5.0/95 is preferred. Ratios will vary depending on the amount of age resister desired to be bound and on the reactivity ratios of the monomers in the particular polymerization system used.

Preferably the monomer system contains at least 50 parts by weight per 100 parts by weight of total monomer of at least one diene, preferably a conjugated diene, such as 1,3-butadiene or isoprene.

One embodiment of the present invention involves the use of a monomer system comprised of from about 50 to about 99.9 parts of at least one diene monomer, preferably a conjugated diene, 0 to about 49.9 parts of at least one monomer selected from the group consisting of vinyl monomers and vinylidene monomers and from about 0.10 to about 5.0 parts by weight of at least one monomeric age resister, all parts being parts by weight per 100 parts by weight of total monomer. Preferably at least 0.5 part of monomeric age resister is used. When at least 0.5 part of the monomeric age resister is used, the upper limit on the diene monomer range is 99.5 parts and the upper limit of the vinyl monomer and/or vinylidene monomer range is 49.5 parts. The upper limit of the monomeric age resister range may be even higher than 5.0, i.e., 10 or 20.

The polymers resulting from the free radical polymerizations of monomeric systems containing the monomeric age resisters of the present invention contain at least one segmeric unit having the following structure:

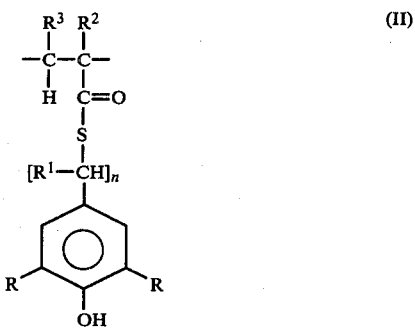

(II)

These polymers, whether liquid or solid, have a special advantage in that the age resistant portion is not extractable, and therefore the polymeric compositions are highly resistant to oxidative aging even after repeated exposure to aqueous detergent solutions or drycleaning fluids. This feature is especially significant where polymers are used in foam backings for rugs and where polymers are used in solution or latex form to treat fabrics, since such products are often exposed to aqueous detergent solutions or drycleaning fluids. This feature is also significant where factors such as contact with lubricating oils or exposure to high vacuum conditions are a consideration.

One of the advantages of the present process is that it permits the preparation of polymers prepared from monomer systems containing diene monomers and containing built-in stabilizers without the formation of appreciable gel, that is, polymers can be made which are essentially gel free.

To afford adequate protection against degradation the polymers should contain from about 0.10 part to about 10.0 parts by weight of the segmeric form of the monomeric age resister per 100 parts by weight of the polymer, although from about 0.50 part to about 5.0 parts is normally satisfactory, from about 0.50 part to about 2.0 part being preferred. As much as 20 parts of the polymer may consist of the age resister segmeric unit while the lower limit may be 0.50 part to 0.10 part and lower.

All of the phenolic compounds described herein, which are novel compounds, are capable of stabilizing polymers by simple incorporation into the polymers by conventional techniques such as by addition to polymer latices or by addition to the solid polymer on a mill or in a Banbury. When blending a self-stabilizing polymer with other polymers, especially when the self-stabilizing polymer contains large amounts of the segmeric form of the monomeric age resister, one must consider the solubility problems involved in blending dissimilar polymers.

Polymers subjected to deterioration by oxidation that can be conveniently protected by the age resisters described herein include substituted and unsubstituted, saturated and unsaturated, natural and synthetic polymers. The oxidizable natural polymers include natural rubber in its various forms, e.g., pale crepe and smoked sheet, and balata and gutta percha. The oxidizable synthetic polymers are prepared from a single monomer (homopolymer) or a mixture of two or more copolymerizable monomer (copolymers) wherein the monomers are combined in a random distribution or block form. The monomers may be substituted or unsubstituted and may possess one or more double bonds, for example, diene monomers, both conjugated and non-conjugated, and monoolefins including cyclic and acyclic monoolefins, especially vinyl and vinylidene monomers.

One of the advantages obtained in chemically combining the monomeric age resisters in the polymers by free radical polymerization techniques, as opposed to physically incorporating the antioxidant, e.g., by addition to the polymer latex or by milling or Banburying techniques, is that the age resister is not extractable.

The following examples illustrate the practice of the present invention. Unless otherwise indicated, all parts are parts by weight.

The contents of U.S. Pat. No. 3,714,122 are incorporated herein by reference with particular emphasis on the disclosures relating to polymerization.

Examples 1, 2 and 3 illustrate the preparation of compounds of the present invention.

EXAMPLE 1

S-[2-(3,5-di-tert.-butyl-4-hydroxyphenyl)ethyl]thiomethacrylate was prepared by dropwise addition of 9.3 grams of methacryloyl chloride to a solution of 19 grams of 2-(3,5-di-tert.-butyl-4-hydroxyphenyl) ethyl mercaptan and 14.4 grams of triethylamine in 75 milliliters of tetrahydrofuran. The temperature rose to 58° C. during the addition. The mixture was stirred for 4 hours at ambient temperature and was then poured into 300 milliliters of water. The organic oil was separated by extraction with hexane. The extract was allowed to evaporate and the residue was allowed to stand until crystallization occurred. After two recrystallizations from hexane the product melted at 82° to 85.5° C.

EXAMPLE 2

S-[3-(3,5-di-tert.-butyl-4-hydroxyphenyl)propyl]thiomethacrylate was prepared by dropwise addition of 13 grams of methacryloyl chloride to a solution of 28 grams of 3-(3,5-di-tert.-butyl-4-hydroxyphenyl)propyl mercaptan and 20.2 grams of triethylamine in 100 milliliters of tetrahydrofuran. The acid chloride was added in 25 minutes. The temperature rose during the addition from 21° C. to 52.5° C. The mixture was stirred for 6 hours at ambient temperature and was then poured into 400 milliliters of water. The organic oil was separated by extraction with hexane and the extract was allowed to evaporate. Some solid crystallized from the residue on prolonged standing. The partially crystalline mixture was stirred with cold hexane and the solid was filtered off. After recrystallization from hexane the product melted at 48° to 52° C.

EXAMPLE 3

S-(3,5-di-tert.-butyl-4-hydroxybenzyl) thiomethacrylate was prepared as follows: Methacryloyl chloride (8.65 grams) was added dropwise over 1 hour at 24° to 28° C. to a solution of 16.7 grams of 3,5-di-tert.-butyl-4-hydroxybenzyl mercaptan and 13.4 grams of triethylamine in 75 milliliters of tetrahydrofuran. The reaction mixture was stirred for 3 hours at room temperature and was then poured into 400 milliliters of water. The yellow oil which precipitated was separated by extraction with hexane. Evaporation of the hexane left 19.9 grams of a pale yellow oil.

The following examples illustrate the preparation of polymers containing monomeric age resisters as part of the polymeric chain. They also illustrate the age resistance possessed by polymers having the monomeric age resisters physically combined therewith. Unless otherwise indicated all parts are parts by weight.

Butadiene, acrylonitrile and monomers of the present invention were polymerized using the following recipe.

| Ingredient | Parts by Weight |
| --- | --- |
| Butadiene | 67 |
| Acrylonitirle | 33 |
| Water | 195 |
| Potassium soap of tallow fatty acids | 2.5 |
| Trisodium phosphate | 0.2 |
| Ferrous sulfate | 0.0144 |
| Chelating agent* | 0.0568 |
| Sodium formaldehyde sulfoxylate | 0.0412 |
| Tert-dodecyl mercaptan | 0.5 |
| Cumene hydroperoxide** | 0.023 |
| Polymerizable antioxidant | 1.5 |

*90/10 mixture of tetrasodium salt of ethylenediamine-tetra-acetic acid and monosodium salt of N,N-di(α-hydroxyethyl) glycine
**70% cumene hydroperoxide in cumene The polymerization reaction was run for 16 hours at 15° C. The resulting latex was coagulated by pouring it into isopropanol.

The use of S-[2-(3,5-di-tert-butyl-4-hydroxyphenyl)ethyl]thiomethacrylate in the above recipe gave a conversion of 56 percent while S-[3-(3,5-di-tert-butyl-4-hydroxyphenyl)propyl]thiomethacrylate gave a conversion of 40 percent.

The polymers were extracted with methanol in a Soxhlet extractor for 48 hours and the extracted polymers were dissolved in benzene. Films were cast from the benzene solutions and oxygen absorption measurements were made on the films. The data are as follows:

| Antioxidant | Hrs. to 1% Oxygen Absorbed (100° C.) |
| --- | --- |
| Example 1 | 328 |
| Example 2 | 383 |

Butadiene, styrene and monomer of the present invention were copolymerized using the following recipe.

| Ingredient | Parts by Weight |
| --- | --- |
| Butadiene | 75 |
| Styrene | 25 |
| Water | 200 |
| Potassium soap of mixed fatty acids | 5 |
| Sodium salt of condensed naphthalene sulfonic acid | 0.08 |
| Trisodium phosphate | 0.25 |
| Ferrous sulfate | 0.0075 |
| Chelating agent | 0.0375 |
| Tert. dodecyl mercaptan | 0.3 |
| Sodium formaldehyde sulfoxylate | 0.025 |
| P-methane hydroperoxide | 0.06 |
| Antioxidant of Example 3 | 1.5 |

After 16 hours at 15° C. 70 percent conversion to polymer was obtained. A film formed from extracted polymer required 381 hours to absorb 1 percent oxygen at 100° C.

Although an initial attempt to polymerize the antioxidant of Example 3 in a butadiene/acrylonitrile recipe was unsuccessful a later attempt was successful using the same recipe. Conversions of 81 to 87 percent were obtained after 16 hours of polymerization.

While certain representative embodiments and details have been shown for the purpose of illustrating the invention it will be apparent to those skilled in this art that various changes and modifications may be made therein without departing from the spirit or scope of the invention.

What I claim is:

1. A compound having the following structural formula:

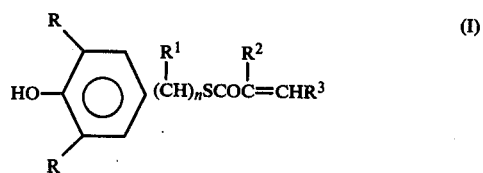

wherein R is a tert. alkyl radical containing 4 to 8 carbon atoms, $R^1$, $R^2$ and $R^3$ are selected from the group consisting of hydrogen, alkyl radicals containing 1 to 4 carbon atoms and wherein n is 1 to 12.

2. The compound of claim 1 wherein R is tert. butyl, $R^1$ is hydrogen, $R^2$ is selected from the group consisting of hydrogen and methyl, $R^3$ is hydrogen and n is 1 to 3.

3. The compound as recited in claim 2, selected from the group consisting of S-[2-(3,5-di-tert.-butyl-4-hydroxyphenyl)ethyl]thiomethacrylate; S-[3-(3,5-di-tert.-butyl-4-hydroxyphenyl)propyl]thiomethacrylate; and S-(3,5-di-tert.-butyl-4-hydroxybenzyl)thiomethacrylate.

* * * * *